United States Patent
Trerotola

(10) Patent No.: US 6,213,976 B1
(45) Date of Patent: Apr. 10, 2001

(54) BRACHYTHERAPY GUIDE CATHETER

(75) Inventor: Scott O. Trerotola, Carmel, IN (US)

(73) Assignee: Advanced Research and Technology Institute, Inc., Indianapolis, IN (US)

( * ) Notice: Subject to any disclaimer, the term of this patent is extended or adjusted under 35 U.S.C. 154(b) by 0 days.

(21) Appl. No.: 09/359,466

(22) Filed: Jul. 22, 1999

(51) Int. Cl.⁷ .................................................. A61M 29/00
(52) U.S. Cl. ............................................................ 604/104
(58) Field of Search ..................................... 604/104, 105, 604/106, 107, 109; 606/191, 197, 198, 199, 200

(56) References Cited

U.S. PATENT DOCUMENTS

| | | |
|---|---|---|
| 4,834,713 | 5/1989 | Suthanthiran . |
| 5,199,939 | 4/1993 | Dake et al. . |
| 5,257,979 | 11/1993 | Jagpal . |
| 5,429,582 | 7/1995 | Williams . |
| 5,498,227 | 3/1996 | Mawad . |
| 5,503,613 | 4/1996 | Weinberger . |
| 5,540,659 | 7/1996 | Teirstein . |
| 5,611,767 | 3/1997 | Williams . |
| 5,618,266 | 4/1997 | Liprie . |
| 5,620,479 | 4/1997 | Diederich . |
| 5,628,770 | 5/1997 | Thome et al. . |
| 5,643,171 | 7/1997 | Bradshaw et al. . |
| 5,653,683 | 8/1997 | D'Andrea . |
| 5,662,580 | 9/1997 | Bradshaw et al. . |
| 5,683,345 | 11/1997 | Waksman et al. . |
| 5,695,479 | 12/1997 | Jagpal . |
| 5,713,828 | 2/1998 | Coniglione . |
| 5,716,595 | 2/1998 | Goldenberg . |
| 5,720,717 | 2/1998 | D'Andrea . |
| 5,851,171 | 12/1998 | Gasson . |
| 5,855,565 | * 1/1999 | Bar-Cohen et al. ................. 604/104 |
| 5,891,091 | 4/1999 | Teirstein . |
| 5,938,582 | 8/1999 | Ciamacco, Jr. et al . |

FOREIGN PATENT DOCUMENTS

WO 96/14898  5/1996  (WO) .

* cited by examiner

*Primary Examiner*—Manuel Mendez
(74) *Attorney, Agent, or Firm*—Leydig, Voit & Mayer, Ltd.

(57) ABSTRACT

A guide catheter includes a body and a centering mechanism. The body has an elongatable section and a lumen with a stop. The centering mechanism is a plurality of bias elements that forms a self-expanding basket attached to the body so that the elongatable section is within the basket. A straightening catheter engages the stop to stretch the elongatable section and to flatten the basket against the body. The guide catheter can be inserted into a vessel and the centering mechanism can be positioned at a desired treatment site by means of an over-the-wire guidewire system. The straightening catheter can be removed to allow the self-expanding basket to center the guide catheter in the vessel. A dosing device can then be inserted into the guide catheter and located at the centered basket to deliver the brachytherapy to prevent restenosis.

43 Claims, 3 Drawing Sheets

BRACHYTHERAPY GUIDE CATHETER

TECHNICAL FIELD OF THE INVENTION

The present invention pertains generally to catheters. More particularly, the present invention relates to guide catheters and methods of using guide catheters, as might be particularly useful for impeding restenosis using brachytherapy.

BACKGROUND OF THE INVENTION

A high plasma concentration of cholesterol, particularly low-density lipoprotein cholesterol, is a primary risk factor for the development of atherosclerosis, an inflammatory disease. Despite growing awareness of the benefits of lifestyle changes, such as implementing exercise programs and following a lower-cholesterol diet, and despite the advent of new drugs designed to lower plasma cholesterol concentrations, cardiovascular disease remains a principal cause of death in the United States.

Stenosis, or stricture, of arteries or veins by the formation of atherosclerotic plaque is a well known and frequent medical problem. Such blockages can be treated by using devices which remove the plaque or by implementing, for example, stents which mechanically maintain the vessel to allow increased blood flow through the artery or vein. The most common procedure, however, is the percutaneous transluminal angioplasty, which is commonly referred to as a "balloon angioplasty."

A balloon angioplasty is performed by inserting a catheter having an inflatable balloon disposed at the distal end of the catheter into an artery or vein. The catheter is positioned so that the uninflated balloon is located at a stenotic site. The balloon is then inflated. The inflated balloon cracks the intima of the atheromatous plaque. Consequently, the artery or vein is dilated and remodeled. After treatment, the balloon is deflated and the catheter is removed.

In most patients, the crack heals, and the remodeled artery or vein adapts to its new size. As a result, the intraluminal passageway is enlarged and blood flow is increased. However, restenosis, that is, the re-constricting of the vessel, occurs in many patients.

Restenosis occurs as a healing response to the injury inflicted to the vessel wall during angioplasty. The repair response is characterized by migration, proliferation, and neointima formation of vascular smooth muscle cells at the site of the angioplasty. The smooth muscle cell accumulation narrows the blood vessel lumen that was opened by the angioplasty. Often an additional angioplasty is administered to ameliorate the effects of the restenosis.

Previous attempts to inhibit restenosis of arteries or veins have had varying degrees of success. One approach involves intravascular delivery of radiation, or brachytherapy, at the site of the angioplasty to cause focal medial fibrosis, thereby impeding restenosis. Intravascular delivery of the irradiation treatment allows for controlled delivery of the dosage and prevents adjacent tissue from being unnecessarily exposed to the radiation source. By way of example, U.S. Pat. No. 5,683,345 to Waksman et al. describes an apparatus and method for delivery of a radiation source through a catheter to a desired site in a coronary artery to inhibit the formation of scar tissue which may occur during restenosis.

The radiation source delivered to the treatment site can take on various forms, one example being "seeds." Regardless of its form, the radiation source emits radiation radially in all directions. An eccentrically located radiation source will deliver unequal amounts of radiation to portions of the vessel wall. In order to minimize unwanted radiation exposure and to maximize the effectiveness of brachytherapy in preventing restenosis, a means of centering the radiation source in the vessel is highly desired.

Previous attempts to provide an apparatus capable of delivering a centered radiation source to a treatment site in a vessel have included, for example, the use of a balloon and/or a wire form for centering. See, for example, the approaches described in U.S. Pat. No. 5,540,659 to Teirstein and U.S. Pat. No. 5,643,171 to Bradshaw.

These previous attempts to center the radiation source in the vessel have not met with success. For example, devices that utilize an inflatable balloon for centering the treatment catheter suffer because the material and shape of the balloon can negatively affect the ability of the balloon to center the catheter in the vessel. In this respect, the curvature of the vessel can be so pronounced that the balloon cannot effectively center the treatment catheter. Another drawback is that when the balloon is inflated to center the catheter, the balloon occludes blood flow in the vessel. The occlusion of blood flow in an artery or vein for a short amount of time (e.g., a minute) can cause discomfort to the patient and, over a longer period may cause more serious injury, such as myocardial infarction. Even with flutes located on the balloon surface, an inflated balloon occludes blood flow significantly.

In addition, conventional devices which use a wire form as a centering means have required an additional step to activate the centering mechanism, such as forcing the wires radially out from the catheter, and additional structure, such as a sheath or a collar. In the latter respect, the structure of conventional wire form centering means is generally complicated thereby often leading to difficulty in construction.

Another significant limitation with previous approaches for centering treatment catheters is that these devices often require the use of a so-called "monorail" guidewire system to allow the treatment channel to be located in the central portion of the catheter. In a monorail guidewire system, the guidewire lumen does not run the longitudinal length of the catheter, but rather runs for only a portion of the catheter. The catheter slides alongside, rather than over, the guidewire. Typically, the monorail guidewire lumen is located eccentrically on the catheter.

Catheters with a monorail guidewire system are difficult to use because, for example, if the monorail catheter meets an obstruction, a further attempt by the user to insert the catheter could cause the catheter to buckle rather than move further into the vessel.

From the foregoing, it will be appreciated that there exists a need in the art for a guide catheter which can be inserted into a vessel with a guidewire system which extends substantially along the longitudinal length of the catheter. There is also a need for a guide catheter which can be centered in the vessel using a simple centering mechanism that allows blood flow to continue, and which can be used to deliver a centered radiation source to a treatment site to prevent restenosis. It is an object of the present invention to provide such a guide catheter that satisfies these needs. These and other objects and advantages of the present invention, as well as additional inventive features, will be apparent from the description of the invention provided herein.

BRIEF SUMMARY OF THE INVENTION

The present invention provides a guide catheter and a method for centering a dosing device, such as a dosing catheter, in a vessel. In particular, the guide catheter of the present invention is provided with a tubular body and a centering mechanism. The body has an outer surface and includes a fixed section, an elongatable section, a lumen, and a stop located within the lumen. The centering mechanism includes a plurality of bias elements. The ends of each bias element are attached to the outer surface of the body so that the elongatable section is between the ends. The bias elements are normally in a resting position such that the bias elements arc radially outward from the body, generally reaching a maximum distance from the body at the midpoint of each bias element. A tensioned position can be reached such that the elongatable section is lengthened and the bias elements are flattened against the outer surface of the guide catheter by inserting a straightening catheter into the lumen of the guide catheter (such that the straightening catheter engages the stop) and further moving the straightening catheter. Disengagement of the straightening catheter from the stop returns the bias elements from the tensioned position to the resting position.

The method for centering a dosing device includes the steps of providing a guide catheter comprising (i) a tubular member having an outer surface, (ii) a plurality of bias elements, each having two ends fixed in a longitudinal spaced relation with each other on the outer surface of the tubular member such that the bias elements are capable of being formed into a range of positions (e.g., resting, tensioned, and intermediate positions), and (iii) means for selectively tensioning the bias elements so that deployment of the means for tensioning converts the bias elements from a first position to a second position, and wherein deactivation of the means for tensioning converts the bias elements to a third position; deploying the means for moving the bias elements to the second position; inserting the guide catheter into a vessel and positioning the centering mechanism at a desired treatment site; disengaging the tensioning means to allow the bias elements to center the guide catheter by moving to the third position established when the bias elements contact the vessel wall; and inserting the dosing device into the centered guide catheter so as to position the dosing device.

Advantageously, the inventive guide catheter can deliver a dosing device to the center of a vessel for treatment such as brachytherapy to prevent restenosis. Significantly, the guide catheter uses a centering mechanism that includes a simple, self-expanding basket (e.g., of a thermoplastic or wire material) and an elongatable section that uses equilibrium principles to center the guide catheter. Furthermore, the basket of the inventive guide catheter allows blood flow to continue even while the centering mechanism is in use to center the guide catheter.

The present invention will be more fully understood upon reading the following detailed description in conjunction with the accompanying drawings.

DETAILED DESCRIPTION

Figure 1:
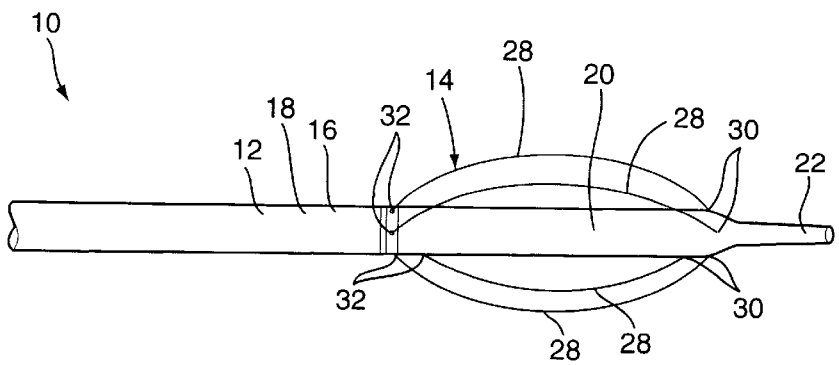
FIG. 1 is a side elevational view of a catheter positioning guide comprising a basket constructed in accordance with the present invention.

Turning now to the Figures, a guide catheter 10, in accordance with the present invention, is shown. The guide catheter 10 includes a hollow body 12 and a centering mechanism 14. The body 12 is tubular and has an outer surface 16. The tubular body 12 can be of any suitable diameter, such as, for example, a diameter of about 2 millimeters to about 4 millimeters, and is desirably sized according to the size of the vessel to be treated. The body 12 includes a fixed section 18, an elongatable section 20, and a tip 22.

The elongatable section 20 is preferably made of an elastomer which is flexible. The material for the section 20 is capable of elongating when tension is applied along the longitudinal axis of the section 20 and also capable of promptly returning to an original length when tension is removed from the section 20. Alternatively, the elongatable section 20 can be made from coiled wire. The fixed section 18 is not readily elongatable but is flexible. The tip 22 is tubular and has a smaller diameter than the rest of the body 12 and serves to protect the guide catheter 10 and to facilitate the insertion, and further movement, of the guide catheter 10 in a vessel. The fixed section 18 and the tip 22 can be made from any suitable catheter material, including thermoplastics such as, for example, nylon, polyethylene, polytetrafluoroethylene, polyvinyl chloride, ethylene-propylene copolymers, and the like, as well as combinations thereof.

The centering mechanism 14 is attached to the outer surface 16 of the body 12 and includes a plurality of bias elements 28 that forms a self-expanding basket (e.g., of a wire or thermoplastic material). Each bias element 28 has a first end 30 and a second end 32. The ends 30, 32 are attached to the outer surface 16 by a known method, such as ultrasonic welding, or through other methods as will be appreciated by one of ordinary skill in the art. As shown in FIG. 1, the elements 28 are arcuate. The bias elements 28 are fixed in a longitudinal spaced relation with each other on the outer surface 16 such that the elements 28 are longitudinally aligned and are radially spaced in a predetermined amount. It is to be noted that, although FIG. 1 shows four bias elements 28, the number of bias elements can be increased or decreased to any suitable number. By way of example, the number of bias elements can range from 2 to about 36.

The elements 28 are attached to the outer surface 16 such that the elongatable section 20 is between the ends 30, 32. The elongatable section 20 can be of any suitable length sufficient to elongate the longitudinal length of the elements. By way of example, and not limitation, the elongatable section can range in length from about 10 mm to about 99 mm. The elements 28 are cooperatively arranged with the elongatable section 20 to allow an external force applied to the former to be distributed to the latter and vice-versa. The cooperative arrangement links the movements of the elongatable section 20 and the elements 28 whereby the step of elongating the section 20 flattens the arc-shape of the elements 28. Conversely, by allowing the elongatable section 20 to return towards its original length (i.e., shortening the elongatable section 20), the radius of the arc-shape of the elements 28 increases.

The bias elements 28 are small diameter filaments that are preferably made of nitinol. Desirably, the bias elements 28 can have any suitable diameter, and preferably the diameter of the bias elements ranges from about 0.010 inches (0.254 mm) to about 0.020 inches (0.508 mm). The elements 28 are uniform in length and can be in a range of lengths, from about 10 to about 100 millimeters long. The elements 28 are preferably sized commensurate with the size of the vessel to be treated. In wire embodiments, the bias elements 28 can be made from another material (aside from nitinol), such as a steel (including a spring steel), so long as the material provides a spring force to maintain the proper arc-shape of the basket while also being elastic, substantially kink-proof, and resistant to breakage.

The bias elements 28 are capable of moving from a resting position to a tensioned position. The elements 28 can also be in an intermediate position, which is any position between the resting position and the tensioned position. In the resting position, the longitudinal distance between the attached ends 30, 32 along the outer surface 16 of the body 12 is less than the circumferential length of the bias elements 28. To move the elements 28 from the resting position to the tensioned position, the section 20 can be elongated.

Figure 2:
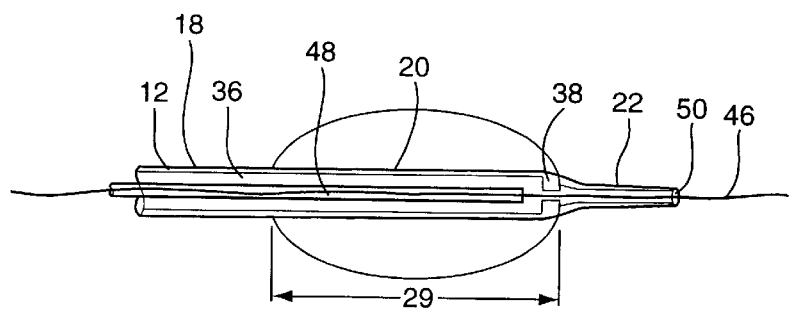
FIG. 2 is an enlarged, fragmentary side view of the catheter positioning guide of FIG. 1 that shows a straightening catheter inserted in the catheter positioning guide.
Figure 3:
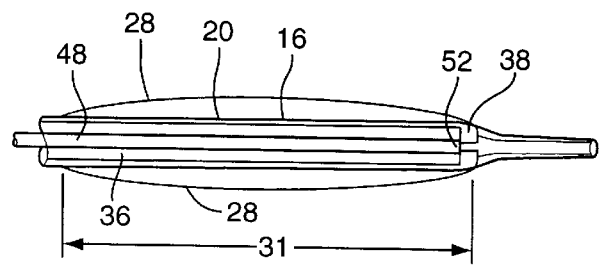
FIG. 3 is an enlarged, fragmentary side view of the catheter positioning guide of FIG. 1 that shows the straightening catheter in contact with stops and that shows the basket partially flattened and an elongatable section of the guide elongated.
Figure 4:
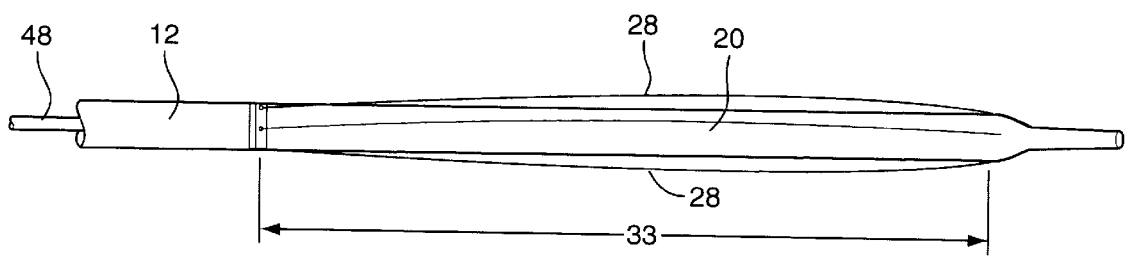
FIG. 4 is an enlarged, fragmentary side view of the catheter positioning guide of FIG. 1 that shows the basket flattened and the elongatable section further elongated.

When the bias elements 28 are moved from the resting position to the tensioned position, the bias elements 28 flatten against the outer surface 16 of the body 12. In the tensioned position, the longitudinal distance between the attached ends 30, 32 along the outer surface 16 of the body 12 is substantially equal to the longitudinal length of the bias elements 28. When the force required to elongate the section 20 is removed, the bias elements 28 return to the original resting position. To illustrate the elongation of section 20, FIG. 2 shows the section 20 having a length 29, which corresponds to the resting position. FIG. 3 shows the section 20 having a length 31, which corresponds to an intermediate position. FIG. 4 shows the section 20 having a length 33, which corresponds to the tensioned position. The length 33 is greater than the length 31, and the length 31 is greater than the length 29.

Referring to FIG. 2, the body 12 also includes a stop 38. A lumen 36 extends substantially through the longitudinal and radial center of the body 12, including the fixed section 18, the elongatable section 20, the stop 38, and the tip 22. The lumen 36 is sized to accommodate the delivery of the radiation source, to allow a guidewire 46 to pass through, and to accept a straightening catheter 48. The lumen 36 is substantially annular in cross-section and has a substantially uniform radius through the sections 18, 20. The stop 38 is a ring-shaped projection which extends radially into the lumen 36. The stop 38 is sized to give the lumen 36 an annular cross-section configured such that the guidewire 46 is able to pass through the stop 38 but the straightening catheter 48 is retained by the stop 38 and prevented from continuing through the lumen 36 to the distal end of the body 12. The annular cross-section of the lumen 36 desirably narrows from the proximate end to the distal end of the tip 22. The lumen 36 terminates at an aperture 50 located at the distal end of the tip 22.

Referring to FIG. 3, to elongate the section 20 and to flatten the elements 28 against the outer surface 16 of the body 12, the straightening catheter 48 is positioned so that a distal end 52 engages the stop 38. Continued insertion of the straightening catheter 48 elongates the section 20. Accordingly, the straightening catheter 48 is made of a relatively rigid catheter material which is sufficiently flexible to be inserted in the vessel while also being capable of elongating the section 20.

The bias elements 28 and the elongatable section 20 are shown in FIGS. 1 and 2 in a resting position. In the resting position, there is no external force applied to the section 20 or to the elements 28 sufficient to move the elements 28 from a generally arc-shape path (e.g., having an enlarged radius) or to elongate the section 20 from an original length. When in the resting position, the elements 28 project radially away from the body 12 such that the ends 30, 32 are attached to the outer surface 16 but the elements 28 arc out from the body 12, reaching a furthest point away from the body 12 at approximately the midpoint of the elements 28.

The elements 28 and the elongatable section 20 are shown in FIG. 3 in an intermediate position. In the intermediate position, an external force is being applied to the section 20 sufficient to elongate the section 20 and to decrease the maximum distance between the bias elements 28 and the body 12 (e.g., decrease the radius of the arc-shape of the elements) but insufficient to move the section 20 and the elements 28 to the tensioned position. When in an intermediate position, i.e., a position between the resting and tensioned positions, the elements 28 are in a corresponding shape between the maximum arcuate shape of the resting position and the minimum linear shape of the tensioned position according to the external force applied to the section 20. As such, the maximum distance between the bias elements 28 and the body 12 is greater in the resting position than in the intermediate position and the maximum distance between the bias elements 28 and the body 12 is greater in the intermediate position than in the tensioned position.

Referring to FIG. 4, the elements 28 and the section 20 are shown in the tensioned position. In the tensioned position, an external force is applied to the section 20 sufficient to elongate the section 20 to a length substantially equivalent to the length of the elements 28. When in the tensioned position, the elements 28 are no longer arced out from the body 12 but rather lay relatively flat (e.g., in a substantially linear path) adjacent the body 12, although some arc can be retained, if desired.

As seen in FIG. 4, the straightening catheter 48 has been inserted to a point where the section 20 has been elongated such that the elements 28 and the section 20 are in the tensioned position. Optionally, once the straightening catheter has been inserted to this tensioned point, the straightening catheter 48 can be locked into place with a locking mechanism, such as, for example, a "Luer" lock (as will be readily apparent to one of ordinary skill in the art), located at the proximate end of the straightening catheter 48.

Figure 5:
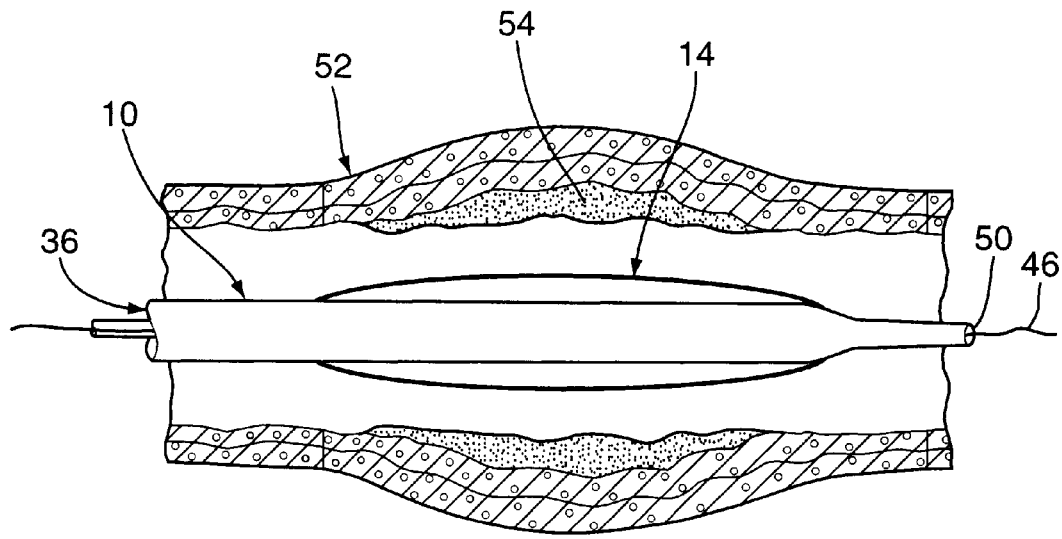
FIG. 5 is a cross-sectional side elevational view of a vessel and a side elevational view of the catheter positioning guide of FIG. 1 with the basket flattened and inserted into the vessel.

In order to use the guide catheter 10 to treat a vessel 52, the user feeds the guidewire 46 into the vessel, as illustrated in FIG. 5. Also, as shown in FIG. 3, the user places the elements 28 and the section 20 in the tensioned position (external to the patient's body) by inserting the straightening catheter 48 into the lumen 36, engaging the stop 38 with the end 52, and elongating the section 20. The straightening catheter 48 is locked in place with the locking mechanism located at the proximate end of the straightening catheter 48.

The user can insert the guide catheter 10 into the vessel 52 by inserting the proximal end of the guidewire 46 into the aperture 50 of the guide catheter 10 and threading the guidewire 46 through the lumen 36. The lumen 36 runs substantially the longitudinal length of the guide catheter 10 and advantageously acts as an "over-the-wire" guidewire channel. The straightening catheter 48 also is preferably adapted to permit threading of the guidewire 46 therethrough, as seen, for example, in FIGS. 2 and 5. As such, a lumen within the straightening catheter 48 preferably acts as an "over-the-wire" guidewire channel over a portion of the guidewire 46 upon entry of the straightener 48 into the guide catheter 10. Once the guidewire 46 is threaded through the lumen, the guide catheter 10 can be inserted into the vessel 52. The centering mechanism 14 can be positioned in the vessel 52 at a desired treatment site 54 by any known method, such as by using a radiopaque marker.

Figure 6:
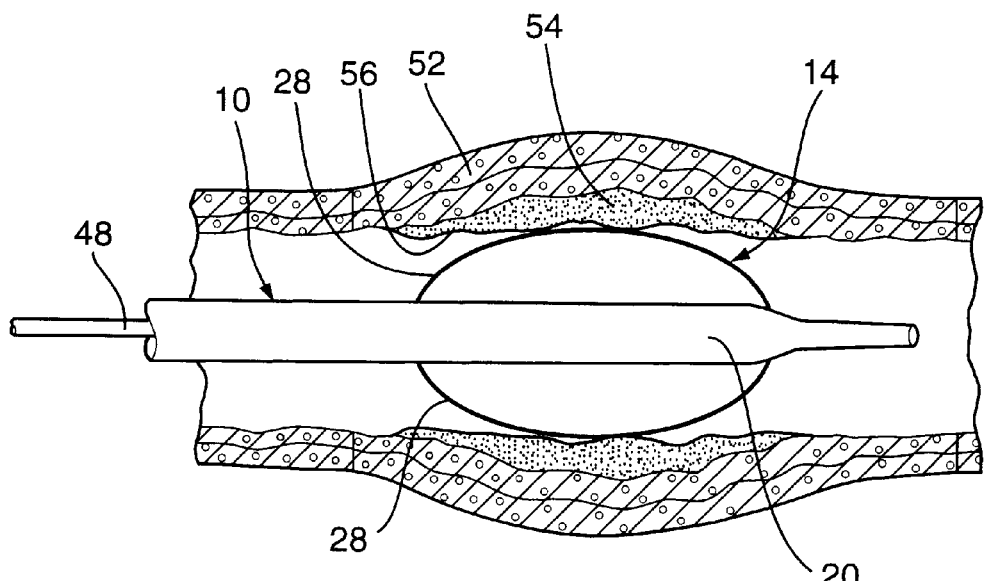
FIG. 6 is a cross-sectional side elevational view of the vessel in FIG. 5 and a side elevational view of the catheter positioning guide of FIG. 1 with the basket in contact with the vessel wall and the guide catheter centered in the vessel.

Referring to FIG. 6, once the centering mechanism 14 is positioned at the desired treatment site 54, the locking mechanism associated with the straightening catheter 48 can be freed to center the centering mechanism 14, and the straightening catheter 48 can be withdrawn such that it disengages the stop 38. With the straightening catheter 48 removed from the stop 38, the bias elements 28 seek to return to the resting position. The elements 28 begin to return to the maximum arc shape, and the section 20 begins to return to its original length. If the elements 28 do not contact any obstruction, the elements 28 continue to arc outward and the section 20 continues to shorten until the resting position is reached. To allow the centering mechanism 14 to center the guide catheter 10, the centering mechanism 14 should be sized for the particular vessel to be treated such that the diameter of the vessel 52 is less than the diameter at the longitudinal midpoint of the elements 28 in the resting position.

In such a situation where the elements 28 and the vessel 52 are properly sized, the elements 28 move from the tensioned position and contact a vessel wall 56 before the elements 28 reach the resting position. The vessel wall 56 applies a normal force to each of the elements 28. The tendency of the elements 28 to move toward their resting position causes them to push against the wall 56, with the wall 56 responding with an equivalent normal force. The wall's 56 normal force is transmitted to the section 20. The elements 28 reach a centered position, i.e., an intermediate position between the resting and the tensioned positions.

Figure 7:
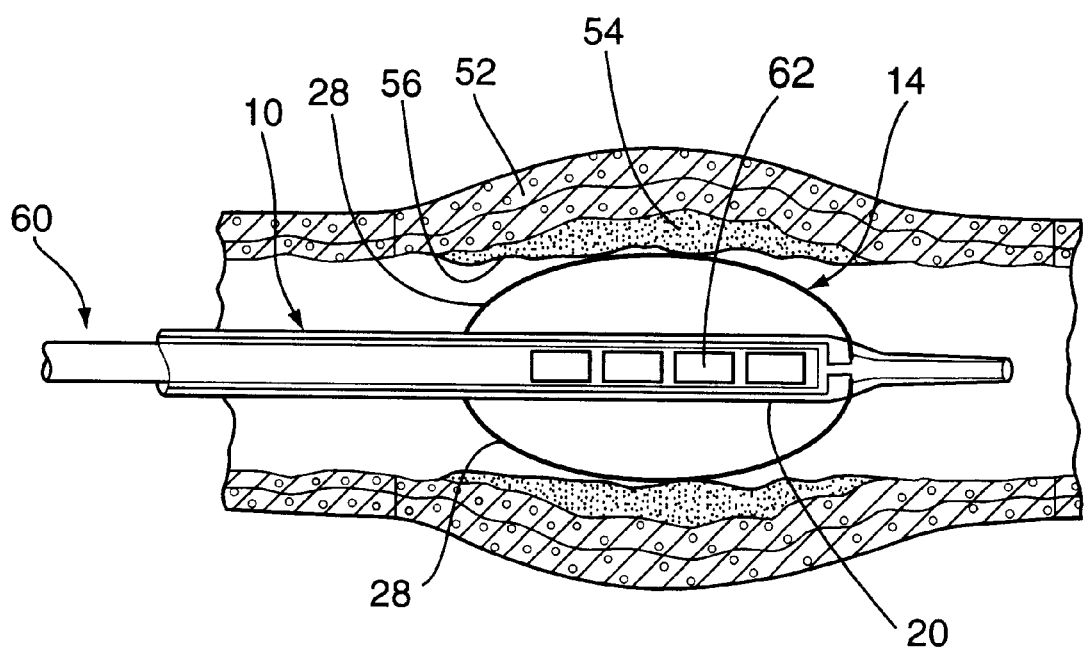
FIG. 7 is a cross-sectional side elevational view of the vessel in FIG. 5 and a side elevational view of the catheter positioning guide of FIG. 1 centered in the vessel with the dosing catheter inserted into the guide catheter and similarly centered in the vessel.

With reference to FIG. 7, a dosing catheter 60 can be inserted into the lumen 36 of the guide catheter 10. The lumen 36 acts as a treatment channel. The guide catheter 10 is centered in the vessel 52 once the equilibrium position is reached. Before inserting the dosing catheter 60, the straightening catheter 48 is withdrawn entirely from the guide catheter 10. The dosing catheter 60 is tubular and has a diameter between about 1 millimeter to about 2 millimeters and is preferably sized according to the diameter of the lumen 36 in sections 18, 20 (see FIG. 2). The dosing catheter 60 contains a radiation source 62. The radiation source 62 can be in any known form, such as a seed or a pellet. Alternatively, the dosing catheter 60 could contain another treatment material, such as a drug.

The dosing catheter 60 is inserted into the guide catheter 10 until the radiation source 62 is located within the centering mechanism 14. The dosing catheter 60 can be inserted in an "over-the-wire" fashion over the guidewire 46 if desired, or alternatively, the dosing catheter 60 can be inserted alongside the guidewire 46. Once the radiation source 62 is within the mechanism 14, the radiation source 62 is centered within the vessel 52. The radiation source 62 is positioned in the centering mechanism 14 for the desired dosage time. Once the desired dosing time has elapsed, the dosing catheter 60 is withdrawn from the guide catheter 10.

To withdraw the guide catheter 10 from the vessel, the straightening catheter 48 is inserted into the lumen 36 of the guide catheter 10 to engage the stop 38 and to elongate the section 20. Once the section 20 and the elements 28 are moved to the tensioned position so that the elements 28 are flattened and substantially linear in shape, the guide catheter 10 can be withdrawn. Alternatively, the guide catheter 10 can be moved to another location in the vessel 52 so that the centering mechanism 14 is positioned at a second desired treatment site. The dosing steps described above can be repeated. This re-positioning procedure can be repeated as many times as desired in the vessel 52.

The lumen 36 is radially centrally disposed in the guide catheter 10 and acts as the guidewire lumen and the treatment channel. Because the lumen 36 runs substantially the longitudinal length of the guide catheter 10, the guide catheter 10 provides an over-the-wire guidewire system, which is particularly advantageous because it allows the guidewire 46 to support and to guide the guide catheter 10 along substantially the entire length of the guide catheter 10.

While this invention has been described with an emphasis upon preferred embodiments, it will be obvious to those of ordinary skill in the art that variations of the preferred embodiments may be used and that it is intended that the invention may be practiced otherwise than is specifically described herein. For example, the bias elements 28 need not take an arced form in the resting and/or intermediate positions, although the arced form is preferable. Accordingly, this invention includes all modifications encompassed within the spirit and scope of the invention as defined by the following claims.

What is claimed is:

1. An apparatus for centering a dosing device in an internal locus comprising:

(a) a tubular member having an outer surface, said tubular member comprising an elongatable section, a non-elongatable but flexible section, and a lumen including a stop therein;

(b) a plurality of bias elements, each having two ends, said plurality of bias elements capable of being formed into a range of positions, wherein the two ends of said plurality of bias elements are fixed in a longitudinal spaced relation with each other on the outer surface of said tubular member such that at least a portion of the elongatable section of said tubular member is between the two ends; and (c) a removable straightening member capable of being selectively inserted into the lumen of said tubular member to engage with the stop, wherein continued advancement of said straightening member upon engagement with the stop causes longitudinal stretching of the elongatable section of the tubular member and converts said plurality of bias elements from a resting position to a tensioned position, and wherein disengagement of said straightening member from the stop at least partially releases the stretching of the elongatable section to cause said plurality of bias elements to convert from the tensioned position to a third position which can be the same or different from the resting position.

2. The apparatus of claim 1, wherein the resting position and the third position are substantially the same.

3. The apparatus of claim 1, wherein the resting position, tensioned position, and third position of the bias elements are each characterized by a maximum distance from said tubular member, and wherein the maximum distance (from said tubular member) of at least one of the bias elements in the third position is intermediate the maximum distance (from said tubular member) of the at least one bias element in the resting position and the maximum distance (from said tubular member) of the at least one bias element in the tensioned position.

4. The apparatus of claim 1, wherein substantially all of the elongatable section is disposed between the two ends of said plurality of bias elements.

5. The apparatus of claim 1, wherein said elongatable section comprises an elastomer.

6. The apparatus of claim 1, wherein said elongatable section comprises a coil.

7. The apparatus of claim 1, wherein said non-elongatable section comprises a thermoplastic selected from the group consisting of nylon, polyethylene, polytetrafluoroethylene, polyvinyl chloride, ethylene-propylene copolymers, and combinations thereof.

8. The apparatus of claim 1, wherein said bias elements comprise nitinol.

9. The apparatus of claim 1, wherein said bias elements comprise steel.

10. The apparatus of claim 1, wherein said bias elements collectively form a basket.

11. The apparatus of claim 1, wherein said internal locus has a substantially annular cross-section.

12. The apparatus of claim 11, wherein said internal locus is a mammalian blood vessel.

13. The apparatus of claim 1, wherein said plurality of bias elements are characterized by a substantially arced form in the resting and third positions.

14. The apparatus of claim 1, wherein said plurality of bias elements are characterized by a substantially linear form in the tensioned position.

15. The apparatus of claim 1, wherein the non-elongatable section and the elongatable section are welded to each other.

16. The apparatus of claim 1, further comprising a guidewire, wherein said guidewire is substantially centrally disposed within said tubular member along a longitudinal axis.

17. The apparatus of claim 1, wherein the diameter of said tubular member is from about 2 mm to about 4 mm.

18. The apparatus of claim 1, wherein the length of said plurality of bias elements is from about 10 mm to about 100 mm.

19. The apparatus of claim 1, wherein the length of the elongatable section of said tubular member is about 10 mm to about 99 mm.

20. The apparatus of claim 1, further comprising a locking mechanism for selectively and releasably locking the straightening member within the tubular member.

21. The apparatus of claim 20, wherein the locking mechanism comprises a Luer lock.

22. The apparatus of claim 1, further comprising a protective tip having an aperture therein to permit passage of a guidewire therethrough.

23. The apparatus of claim 22, wherein the protective tip has a smaller diameter than the diameter of said tubular member.

24. The apparatus of claim 1, further comprising a removable dosing catheter capable of being inserted into said tubular member, wherein said dosing catheter is utilized to selectively deliver treatment material to said internal locus.

25. The apparatus of claim 24, wherein the treatment material comprises at least one radioactive element.

26. The apparatus of claim 25, wherein the radioactive element comprises at least one seed.

27. The apparatus of claim 24, wherein the treatment material comprises a drug.

28. The apparatus of claim 24, wherein said dosing catheter has a diameter of from about 1 mm to about 2 mm.

29. An apparatus for centering a dosing device in an internal locus comprising:
a) a tubular member having an outer surface;
b) a plurality of bias elements, each having two ends, said plurality of bias elements capable of being formed into a range of resting, intermediate and tensioned positions, wherein the two ends of said plurality of bias elements are fixed in a longitudinal spaced relation with each other on the outer surface of said tubular member; and
c) means for selectively tensioning said bias elements, wherein deployment of said means for tensioning converts said bias elements from a resting position to a tensioned position and deactivation of said means for tensioning converts said bias elements from the tensioned position to the intermediate position, which can be the same or different from the resting position.

30. The apparatus of claim 29, wherein said bias elements form a generally arc-shaped path while in the resting and intermediate positions characterized by a first radius and a second radius, respectively, and wherein said bias elements in said tensioned position form a substantially linear shape or form a generally arc-shaped path characterized by a third radius that is smaller than the first and second radii.

31. The apparatus of claim 29, wherein the resting position and the intermediate position are substantially the same.

32. The apparatus of claim 29, wherein the resting position, tensioned position, and intermediate position of the bias elements are each characterized by a maximum distance from said tubular member, wherein the maximum distance of the bias elements (from said tubular member) in the intermediate position is intermediate the maximum distance of the bias elements (from said tubular member) in the resting position and the maximum distance of the bias elements (from said tubular member) in the tensioned position.

33. The apparatus of claim 29, wherein said bias elements comprise nitinol.

34. The apparatus of claim 29, further comprising a guidewire, wherein said guidewire is substantially centrally disposed within said tubular member along a longitudinal axis.

35. The apparatus of claim 29, wherein said locus is a mammalian blood vessel.

36. The apparatus of claim 29, further comprising a removable dosing catheter capable of being inserted into said tubular member, wherein said dosing catheter is utilized to selectively deliver treatment material to said internal locus.

37. The apparatus of claim 36, wherein the treatment material comprises a radioactive element.

38. The apparatus of claim 29, wherein said tubular member comprises an elongatable section and a non-elongatable section such that at least a portion of the elongatable section is between the two ends of said bias elements.

39. A method for centering a dosing device in a mammalian blood vessel comprising the steps of:
(a) providing a guide catheter comprising (i) a tubular member having an outer surface, (ii) a plurality of bias elements, each having two ends, fixed in a longitudinal spaced relation with each other on the outer surface of the tubular member, wherein the bias elements are capable of being formed into a range of positions, and (iii) means for selectively tensioning the bias elements so that deployment of the means for tensioning converts the bias elements from a first position characterized by a first maximum distance (from said tubular member) to a second position characterized by a second maximum distance (from said tubular member) that is smaller than the first maximum distance, and wherein deactivation of the means for tensioning converts the bias elements to a third position;

(b) deploying the means for tensioning the bias elements so that the bias elements are converted from the first position to the second position;

(c) inserting the guide catheter into the blood vessel until reaching a desired treatment site;

(d) deactivating the means for tensioning the bias elements so that the bias elements are converted from the second position to the third position having a third maximum distance (from said tubular member) that is greater than the maximum distance of the second position so that the guide catheter is centrally disposed within the blood vessel at or near the desired treatment site; and (e) inserting the dosing device within the guide catheter.

40. The method of claim 39, further comprising the step of:

(f) treating the blood vessel treatment site with at least one treatment material.

41. The method of claim 40, further comprising the steps of:

(g) removing the dosing device from the guide catheter;

(h) deploying the means for tensioning the bias elements so that the bias elements are converted from the third position to a fourth position having a fourth maximum distance to said tubular member that is smaller than the maximum distance of the third position;

(i) moving the guide catheter to a second treatment site in the blood vessel;

(j) deactivating the means for tensioning the bias elements so that the bias elements are converted from the fourth position to a fifth position having a maximum distance (from said tubular member) greater than the maximum distance of the fourth position so that the guide catheter is centrally disposed within the blood vessel at or near the second treatment site;

(k) inserting the dosing device into the guide catheter; and (l) treating the second blood vessel treatment site with at least one treatment material.

42. The method of claim 41, wherein the treatment material comprises at least one radioactive element.

43. The method of claim 41, wherein the second position and the fourth position are the same.

* * * * *